United States Patent
Collins et al.

(10) Patent No.: US 9,066,771 B2
(45) Date of Patent: *Jun. 30, 2015

(54) MODULAR IMPLANT WITH SECURED POROUS PORTION

(71) Applicant: Zimmer Dental, Inc., Carlsbad, CA (US)

(72) Inventors: Michael Scott Collins, San Marcos, CA (US); Harold C Flynn, Jr., Carlsbad, CA (US); Jane Murray, San Marcos, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/010,786

(22) Filed: Aug. 27, 2013

(65) Prior Publication Data

US 2013/0344459 A1    Dec. 26, 2013

Related U.S. Application Data

(63) Continuation of application No. 12/167,088, filed on Jul. 2, 2008, now Pat. No. 8,562,348.

(51) Int. Cl.
  *A61C 8/00* (2006.01)
  *A61C 8/02* (2006.01)
  *A61K 6/02* (2006.01)
  *A61K 6/027* (2006.01)
  *A61K 6/04* (2006.01)
  *A61K 6/08* (2006.01)

(52) U.S. Cl.
  CPC ............. *A61C 8/0037* (2013.01); *A61C 8/0012* (2013.01); *A61C 8/0018* (2013.01);

(Continued)

(58) Field of Classification Search
  CPC ...... A61C 8/00; A61C 8/0022; A61C 8/0021; A61C 8/0037; A61C 8/0075; A61C 8/0012; A61C 8/0018; A61C 8/0013; A61C 8/0006; A61K 6/04; A61K 6/08; A61K 6/024; A61K 6/027
  USPC .................................................. 433/172–176
  See application file for complete search history.

(56) References Cited

U.S. PATENT DOCUMENTS 2,721,387 A    10/1955   Ashuckian
3,314,420 A     4/1967   Smith et al.

(Continued)

FOREIGN PATENT DOCUMENTS

AU    760524 B2    4/2000
CA    2506845 A1   7/2004

(Continued)

OTHER PUBLICATIONS

"U.S. Appl. No. 12/167,088, Advisory Action mailed Jun. 29, 2011", 3 pgs.

(Continued)

*Primary Examiner* — Heidi M Eide
(74) *Attorney, Agent, or Firm* — Schwegman Lundberg & Woessner, P.A.

(57) ABSTRACT

A modular implant includes a head, an intermediate part configured to engage bone, and an initially separate anchor configured to engage the head so that at least the head and the anchor cooperatively secure the intermediate part on the implant to form the modular implant. At least one of the head, the intermediate part, and the anchor has a plurality of forms, and each form is configured to be assembled on at least one form of the other two of the head, intermediate part, and anchor. The intermediate part may include a porous metal such as tantalum.

17 Claims, 5 Drawing Sheets

(52) U.S. Cl.
CPC ....... *A61C 8/0022* (2013.01); *A61C 2008/0046* (2013.01); *A61C 8/0006* (2013.01); *A61C 8/0013* (2013.01); *A61C 8/0075* (2013.01); *A61K 6/024* (2013.01); *A61K 6/027* (2013.01); *A61K 6/04* (2013.01); *A61K 6/08* (2013.01)

(56) References Cited

U.S. PATENT DOCUMENTS

| | | |
|---|---|---|
| 3,423,830 A | 1/1968 | Halpern et al. |
| 3,423,831 A | 1/1968 | Semmelman |
| 3,497,953 A | 3/1970 | Weissman |
| 3,685,115 A | 8/1972 | Scott |
| 3,713,860 A | 1/1973 | Auskern |
| 3,740,851 A | 6/1973 | Weissman |
| 3,797,113 A | 3/1974 | Brainin |
| 3,849,887 A | 11/1974 | Brainin |
| 3,896,547 A | 7/1975 | Kulwiec |
| 3,905,109 A | 9/1975 | Cohen et al. |
| 3,906,550 A | 9/1975 | Rostoker et al. |
| 3,919,773 A | 11/1975 | Freeman |
| 3,934,347 A | 1/1976 | Lash et al. |
| 3,992,725 A | 11/1976 | Homsy |
| 4,011,602 A | 3/1977 | Rybicki et al. |
| 4,016,651 A | 4/1977 | Kawahara et al. |
| 4,086,701 A | 5/1978 | Kawahara et al. |
| 4,097,935 A | 7/1978 | Jarcho |
| 4,122,605 A | 10/1978 | Hirabayashi et al. |
| 4,131,597 A | 12/1978 | Bluethgen et al. |
| 4,178,686 A | 12/1979 | Riess et al. |
| 4,195,366 A | 4/1980 | Jarcho et al. |
| 4,199,864 A | 4/1980 | Ashman |
| 4,229,170 A | 10/1980 | Perez |
| 4,244,689 A | 1/1981 | Ashman |
| 4,252,525 A | 2/1981 | Child |
| 4,259,072 A | 3/1981 | Hirabayashi |
| 4,281,991 A | 8/1981 | Michi et al. |
| 4,321,042 A | 3/1982 | Scheicher |
| 4,375,967 A | 3/1983 | Schaefer |
| 4,379,694 A | 4/1983 | Riess |
| 4,381,918 A | 5/1983 | Ehrnford |
| 4,411,624 A | 10/1983 | Ogino et al. |
| 4,431,420 A | 2/1984 | Adair |
| 4,439,152 A | 3/1984 | Small |
| 4,448,758 A | 5/1984 | Nagai et al. |
| 4,475,892 A | 10/1984 | Faunce |
| 4,478,904 A | 10/1984 | Ducheyne et al. |
| 4,483,678 A | 11/1984 | Nishio et al. |
| 4,492,577 A | 1/1985 | Farris et al. |
| 4,531,915 A | 7/1985 | Tatum, Jr. |
| 4,531,916 A * | 7/1985 | Scantlebury et al. ......... 433/173 |
| 4,536,158 A | 8/1985 | Bruins et al. |
| 4,548,959 A | 10/1985 | Nagai et al. |
| 4,556,534 A | 12/1985 | Burnett et al. |
| 4,708,652 A | 11/1987 | Fujiu et al. |
| 4,713,006 A | 12/1987 | Hakamatsuka et al. |
| 4,722,688 A | 2/1988 | Lonca |
| 4,731,085 A | 3/1988 | Koch |
| 4,737,411 A | 4/1988 | Graves et al. |
| 4,743,260 A | 5/1988 | Burton |
| 4,744,757 A | 5/1988 | Adair et al. |
| 4,744,759 A | 5/1988 | Bowen |
| 4,820,157 A | 4/1989 | Salvo |
| 4,842,517 A | 6/1989 | Kawahara et al. |
| 4,871,384 A | 10/1989 | Kasuga |
| 4,872,839 A | 10/1989 | Branjnovic |
| 4,872,840 A * | 10/1989 | Bori ................ 433/173 |
| 4,877,400 A | 10/1989 | Holsclaw |
| 4,880,610 A | 11/1989 | Constantz |
| 4,906,190 A | 3/1990 | Michna |
| 4,909,738 A | 3/1990 | Ai et al. |
| 4,915,628 A | 4/1990 | Linkow et al. |
| 4,957,554 A | 9/1990 | Mathers et al. |
| 4,957,819 A | 9/1990 | Kawahara et al. |
| 4,960,733 A | 10/1990 | Kasuga et al. |
| 4,969,817 A | 11/1990 | Hiranuma et al. |
| 4,983,182 A | 1/1991 | Kijima et al. |
| 5,000,685 A | 3/1991 | Brajnovic |
| 5,002,488 A | 3/1991 | Homsy |
| 5,004,421 A | 4/1991 | Lazarof |
| 5,007,835 A | 4/1991 | Valen |
| 5,009,709 A | 4/1991 | Ibsen et al. |
| 5,015,186 A | 5/1991 | Detsch |
| 5,049,074 A | 9/1991 | Otani et al. |
| 5,055,497 A | 10/1991 | Okada et al. |
| 5,061,285 A | 10/1991 | Koch |
| 5,062,798 A | 11/1991 | Tsuge et al. |
| 5,064,731 A | 11/1991 | Miyazaki et al. |
| 5,076,789 A | 12/1991 | Tanaka |
| 5,087,200 A | 2/1992 | Branjovic et al. |
| 5,120,340 A | 6/1992 | Ducheyne et al. |
| 5,123,844 A | 6/1992 | Wakai et al. |
| 5,125,839 A | 6/1992 | Ingber et al. |
| 5,125,971 A | 6/1992 | Nonami et al. |
| 5,139,424 A | 8/1992 | Yli-Urpo |
| 5,152,687 A | 10/1992 | Amino |
| 5,176,747 A | 1/1993 | Panzera et al. |
| 5,180,303 A | 1/1993 | Hornburg et al. |
| 5,186,626 A | 2/1993 | Tanaka |
| 5,192,325 A | 3/1993 | Kijima et al. |
| 5,194,000 A | 3/1993 | Dury |
| 5,194,001 A | 3/1993 | Salvo |
| 5,199,873 A | 4/1993 | Schulte et al. |
| 5,205,745 A | 4/1993 | Kamiya et al. |
| 5,232,365 A | 8/1993 | Ikehara |
| 5,232,878 A | 8/1993 | Kasuga et al. |
| 5,236,458 A | 8/1993 | Ducheyne et al. |
| 5,238,405 A | 8/1993 | Marlin |
| 5,254,005 A | 10/1993 | Zuest |
| 5,282,861 A | 2/1994 | Kaplan |
| 5,282,863 A | 2/1994 | Burton |
| 5,288,232 A | 2/1994 | Panzera et al. |
| 5,306,673 A | 4/1994 | Hermansson et al. |
| 5,308,391 A | 5/1994 | Komma et al. |
| 5,310,343 A | 5/1994 | Hasegawa et al. |
| 5,312,254 A | 5/1994 | Rosenlicht |
| 5,314,334 A | 5/1994 | Panzera et al. |
| 5,342,201 A | 8/1994 | Oden |
| 5,344,318 A | 9/1994 | Wilson et al. |
| 5,344,457 A | 9/1994 | Pilliar et al. |
| 5,346,397 A | 9/1994 | Braiman |
| 5,360,448 A | 11/1994 | Thramann |
| 5,368,483 A | 11/1994 | Sutter |
| 5,415,546 A | 5/1995 | Cox, Sr. |
| 5,419,702 A | 5/1995 | Beaty et al. |
| 5,425,639 A | 6/1995 | Anders |
| 5,425,640 A | 6/1995 | Scharf |
| 5,439,380 A | 8/1995 | Marlin |
| 5,443,515 A | 8/1995 | Cohen et al. |
| 5,449,291 A | 9/1995 | Lueschen et al. |
| 5,468,544 A | 11/1995 | Marcolongo et al. |
| 5,470,230 A | 11/1995 | Daftary et al. |
| 5,476,383 A | 12/1995 | Beaty et al. |
| 5,549,123 A | 8/1996 | Okuyama et al. |
| 5,554,665 A | 9/1996 | Tateosian et al. |
| 5,562,733 A | 10/1996 | Weissbach et al. |
| 5,571,016 A | 11/1996 | Ingber et al. |
| 5,572,652 A | 11/1996 | Robusto et al. |
| 5,575,652 A | 11/1996 | Gaffar et al. |
| 5,584,693 A | 12/1996 | Nishihara |
| 5,591,030 A | 1/1997 | Thiel et al. |
| 5,612,049 A | 3/1997 | Li et al. |
| 5,614,330 A | 3/1997 | Panzera et al. |
| 5,621,035 A | 4/1997 | Lyles et al. |
| 5,624,262 A | 4/1997 | Yarovesky et al. |
| 5,645,934 A | 7/1997 | Marcolongo et al. |
| 5,674,069 A | 10/1997 | Osorio |
| 5,676,745 A | 10/1997 | Kelly et al. |
| 5,683,249 A | 11/1997 | Ibsen et al. |
| 5,685,714 A | 11/1997 | Beaty et al. |
| 5,695,337 A | 12/1997 | Tyszblat Sadoun |
| 5,697,785 A | 12/1997 | Delahaye |
| 5,697,976 A | 12/1997 | Chesterfield et al. |
| 5,697,997 A | 12/1997 | Aronsson et al. |
| 5,698,019 A | 12/1997 | Frank et al. |

| Patent | Date | Name |
|---|---|---|
| 5,702,486 A | 12/1997 | Craig et al. |
| 5,713,994 A | 2/1998 | Kramer et al. |
| 5,723,007 A | 3/1998 | Engel et al. |
| 5,727,943 A | 3/1998 | Beaty et al. |
| 5,755,809 A | 5/1998 | Cohen et al. |
| 5,759,036 A | 6/1998 | Hinds |
| 5,762,500 A | 6/1998 | Lazarof |
| 5,772,438 A | 6/1998 | Deom |
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann, geb. Roth et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,947,893 A | 9/1999 | Agrawal et al. |
| 5,951,290 A | 9/1999 | Ardizio et al. |
| 5,951,293 A | 9/1999 | Billet et al. |
| 5,951,295 A | 9/1999 | Lyles et al. |
| 5,961,328 A | 10/1999 | Somborac et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,214,368 B1 | 4/2001 | Lee et al. |
| 6,224,662 B1 | 5/2001 | Nemeth |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,458 B1 | 1/2002 | Schweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,461,160 B1 * | 10/2002 | Sutter ............................ 433/173 |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,537,070 B1 | 3/2003 | Stucki-McCormick |
| 6,540,784 B2 | 4/2003 | Barlow et al. |
| 6,572,373 B2 | 6/2003 | Tramonte |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinhoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 7,011,522 B2 | 3/2006 | Panzera et al. |
| 7,291,012 B2 | 11/2007 | Lyren |
| 8,057,230 B1 * | 11/2011 | Folsom, Jr. .................... 433/174 |
| 8,562,348 B2 | 10/2013 | Collins et al. |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli, Jr. et al. |
| 2004/0024081 A1 | 2/2004 | Trieu et al. |
| 2004/0058299 A1 | 3/2004 | Molin et al. |
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0122431 A1 | 6/2004 | Biedermann et al. |

| | | | |
|---|---|---|---|
| 2004/0131562 A1 | 7/2004 | Gower et al. | |
| 2004/0152034 A1 | 8/2004 | Cummings et al. | |
| 2004/0170946 A1 | 9/2004 | Lyren | |
| 2004/0197737 A1 | 10/2004 | Uckelmann et al. | |
| 2004/0234925 A1 | 11/2004 | Benhamou | |
| 2004/0241614 A1 | 12/2004 | Goldberg et al. | |
| 2005/0014108 A1 | 1/2005 | Wohrle et al. | |
| 2005/0023710 A1 | 2/2005 | Brodkin et al. | |
| 2005/0028424 A1 | 2/2005 | Poinski | |
| 2005/0031704 A1 | 2/2005 | Ahn | |
| 2005/0084533 A1 | 4/2005 | Howdle et al. | |
| 2005/0084819 A1 | 4/2005 | Sims et al. | |
| 2005/0084821 A1 | 4/2005 | Sims et al. | |
| 2005/0096652 A1 | 5/2005 | Burton | |
| 2005/0100724 A1 | 5/2005 | Seargeant | |
| 2005/0109060 A1 | 5/2005 | Cummings et al. | |
| 2005/0123672 A1 | 6/2005 | Justin et al. | |
| 2005/0136378 A1* | 6/2005 | Ennajimi et al. | 433/173 |
| 2005/0184134 A1 | 8/2005 | Charlebois et al. | |
| 2005/0191248 A1 | 9/2005 | Hunter et al. | |
| 2005/0221259 A1 | 10/2005 | Anderson | |
| 2005/0261795 A1 | 11/2005 | Ghosh et al. | |
| 2005/0266382 A1 | 12/2005 | Soler et al. | |
| 2006/0075826 A1 | 4/2006 | Roberts et al. | |
| 2007/0015110 A1 | 1/2007 | Zhang et al. | |
| 2007/0111165 A1 | 5/2007 | Wallick et al. | |
| 2007/0118221 A1 | 5/2007 | Robie et al. | |
| 2007/0148621 A1 | 6/2007 | Yakir | |
| 2007/0184265 A1 | 8/2007 | Ranganathan et al. | |
| 2008/0050699 A1 | 2/2008 | Zhang et al. | |
| 2008/0241793 A1 | 10/2008 | Collins et al. | |
| 2009/0036908 A1* | 2/2009 | Zokol et al. | 606/151 |
| 2009/0098510 A1 | 4/2009 | Zhang | |
| 2009/0098511 A1 | 4/2009 | Zhang | |
| 2010/0003638 A1 | 1/2010 | Collins et al. | |

FOREIGN PATENT DOCUMENTS

| | | | |
|---|---|---|---|
| DE | 4209569 A1 | 11/1994 | |
| DE | 19529036 A1 | 3/1997 | |
| EP | 0266313 A2 | 5/1988 | |
| EP | 0271236 A1 | 6/1988 | |
| EP | 0345581 A2 | 12/1989 | |
| EP | 0417018 A1 | 3/1991 | |
| EP | 0467948 A1 | 1/1992 | |
| EP | 0498923 A1 | 8/1992 | |
| EP | 0333503 A2 | 2/1993 | |
| EP | 0560279 A1 | 9/1993 | |
| EP | 0806211 A1 | 11/1997 | |
| EP | 1281372 A1 | 2/2003 | |
| EP | 1598028 A1 | 11/2005 | |
| EP | 0950421 B1 | 10/2006 | |
| EP | 1712205 A2 | 10/2006 | |
| EP | 1526780 B1 | 1/2008 | |
| GB | 1526780 A | 9/1978 | |
| GB | 2401867 A | 11/2004 | |
| GB | 2416996 A1 | 2/2006 | |
| JP | 61275205 A | 12/1986 | |
| JP | 63290559 A | 11/1988 | |
| JP | 1025849 A | 1/1989 | |
| JP | 2002126071 A | 5/2002 | |
| WO | WO-8900410 A1 | 1/1989 | |
| WO | WO-9011979 A1 | 10/1990 | |
| WO | WO-0366018 B1 | 5/1993 | |
| WO | WO-9320773 A1 | 10/1993 | |
| WO | WO-9421190 A1 | 9/1994 | |
| WO | WO-9528973 A1 | 11/1995 | |
| WO | WO-9721393 A1 | 6/1997 | |
| WO | WO-9741809 A1 | 11/1997 | |
| WO | WO-9830170 A1 | 7/1998 | |
| WO | WO-0021455 A1 | 4/2000 | |
| WO | WO-0132072 A2 | 5/2001 | |
| WO | WO-0187193 A1 | 11/2001 | |
| WO | WO-0234155 A1 | 5/2002 | |
| WO | WO-0236039 A1 | 5/2002 | |
| WO | WO-02062901 A1 | 8/2002 | |
| WO | WO-02064100 A1 | 8/2002 | |
| WO | WO-03065939 A1 | 8/2003 | |
| WO | WO-03065996 A2 | 8/2003 | |
| WO | WO-03078508 A1 | 9/2003 | |
| WO | WO-03094774 A1 | 11/2003 | |
| WO | WO-2004054464 A2 | 7/2004 | |
| WO | WO-2004103202 A1 | 12/2004 | |
| WO | WO-2006082610 A2 | 8/2006 | |
| WO | WO-2006107292 A1 | 10/2006 | |
| WO | WO-2007027794 A1 | 3/2007 | |
| WO | WO-2007086832 A2 | 8/2007 | |
| WO | WO-2010002664 A1 | 1/2010 | |

OTHER PUBLICATIONS

"U.S. Appl. No. 12/167,088, Examiner Interview Summary mailed Jan. 13, 2011", 3 pgs.

"U.S. Appl. No. 12/167,088, Final Office Action mailed Mar. 31, 2011", 17 pgs.

"U.S. Appl. No. 12/167,088, Non Final Office Action mailed Oct. 19, 2010", 13 pgs.

"U.S. Appl. No. 12/167,088, Non Final Office Action mailed Dec.17, 2012", 8 pgs.

"U.S. Appl. No. 12/167,088, Notice of Allowance mailed Jul. 1, 2013", 8 pgs.

"U.S. Appl. No. 12/167,088, Response filed Jan. 24, 2011 to Non Final Office Action mailed Oct. 19, 2010", 18 pgs.

"U.S. Appl. No. 12/167,088, Response filed Apr. 17, 2013 to Non Final Office Action mailed Dec. 17, 2012", 10 pgs.

"U.S. Appl. No. 12/167,088, Response filed Jun. 14, 2011 to Final Office Action mailed Mar. 31, 2011", 11 pgs.

"U.S. Appl. No. 12/167,088, Response filed Oct. 7, 2010 to Restriction Requirement mailed Sep. 21, 2010", 7 pgs.

"U.S. Appl. No. 12/167,088, Restriction Requirement mailed Sep. 21, 2010", 5 pgs.

"European Application Serial No. 09744565.4, Response filed Mar. 28, 2011 to Office Action mailed Feb. 18, 2011", 8 pgs.

"European Application Serial No. 09774115.1, Examination Notification Art. 94(3) mailed Apr. 2, 2013", 5 pgs.

"European Application Serial No. 09774115.1, Non Final Office Action mailed Mar. 23, 2011", 1 pg.

"European Application Serial No. 09774115.1, Non Final Office Action mailed Nov. 12, 2010", 3 pgs.

"European Application Serial No. 09774115.1, Office Action mailed Feb. 18, 2011", 2 pgs.

"Flocculants, Binders, and Bonds", Chapter 11, Molecular Binders, (1995), 173-177.

"International Application Serial No. PCT/US2006/020130, International Search Report mailed Feb. 6, 2007", 7 pgs.

"International Application Serial No. PCT/US2006/033893, International Search Report mailed Jan. 29, 2007", 1 pg.

"International Application Serial No. PCT/US2007/069562, International Search Report mailed Jul. 7, 2008", 4 pgs.

"International Application Serial No. PCT/US2008/074616, International Search Report mailed Dec. 16, 2008", 4 pgs.

"International Application Serial No. PCT/US2008/074642, International Search Report mailed Feb. 12, 2009", 4 pgs.

"International Application Serial No. PCT/US2008/074645, International Search Report mailed Dec. 29, 2008", 9 pgs.

"International Application Serial No. PCT/US2008/074655, International Search Report mailed Feb. 18, 2009", 9 pgs.

"International Application Serial No. PCT/US2009/048456, International Search Report mailed Apr. 27, 2010", 5 pgs.

"International Application Serial No. PCT/US2009/048469, International Search Report and Written Opinion mailed Oct. 19, 2009", 9 pgs.

"International Application Serial No. PCT/US2009/048476, International Preliminary Report on Patentability mailed Jan. 5, 2011", 6 pgs.

"International Application Serial No. PCT/US2009/048476, International Search Report mailed Dec. 10, 2009", 13 pgs.

"International Application Serial No. PCT/US2009/048476, Written Opinion mailed Dec. 10, 2009", 6 pgs.

"International Application Serial No. PCT/US2009/048481, International Search Report mailed Dec. 10, 2009", 13 pgs.

"International Application Serial No. PCT/US2009/062308, International Search Report mailed Jan. 21, 2010", 9 pgs.

"PEEK-CLASSIX", Information Sheet Invibio Ltd., Properties of PEEK-CLASSIX White Granular, (Nov. 2003), 2 pgs.

"The Clinical Assessment of a Ceramic-Coated Transmucosal Dental Implant Collar", International Journal of Prosthodonics vol. 9, Issue 5, (1996), 466-472.

"Two Applications of Transmucosal Milled Ceramic in Implantology", Preliminary Clinical Examples; Implant Quintessence International vol. 27, Issue 8, (1996), 533-548.

Cass, Richard B, et al., "Innovative Ceramic-Fiber Technology Energizes Advanced Cerametrics", The American Ceramic Society, American Ceramic Society Bulletin, (Nov. 2003), 9701-9706.

Ganz, Scott D, "Presurgical Planning With CT-Derived Fabrication of Surgical Guides", J Oral Maxiofac Surg 63, Suppl 2, (2005), 59-73 pgs.

Kan, Joseph Y K, "Computer-Guided Immediate Provisionalization of Anterior Multiple Adjacent Implants: Surgical and Prosthodontic Rationale", Practical Procedures & Aethetic Dentistry, vol. 18, No. 10, (2006), 617-623 pgs.

Matinlinna, Jukka P, et al., "An Introduction to Silanes and Their Clinical Applications in Dentistry", The International Journal of Prosthodontics, vol. 17, No. 2, (2004), 155-164.

Reed, James S., "Chapter 24, Injection Molding", Principles of Ceramics Processing, 2nd Edition, New York : Wiley, (1995), 477-481.

Rosenfeld, Alan L, "Prosthetically Directed Implant Placement Using Computer Software to Ensure Precise Placement and Predictable Prosthetic Outcomes. Part 1: Diagnostics, Imaging, and Collaborative Accountability", International Journal of Periodontics & Restorative Dentistry, vol. 26, No. 3, (2006), 215-221 pgs.

Zhou, Yan, et al., "Shape Optimization of Randomly Oriented Short Fibers for Bone Cement Reinforcements", Materials Science & Engineering A 393, (2005), 374-381.

"European Application Serial No. 09774115.1, Response filed Aug. 12, 2013 to Examination Notification Art. 94(3) mailed Apr. 2, 2013", 21 pgs.

\* cited by examiner

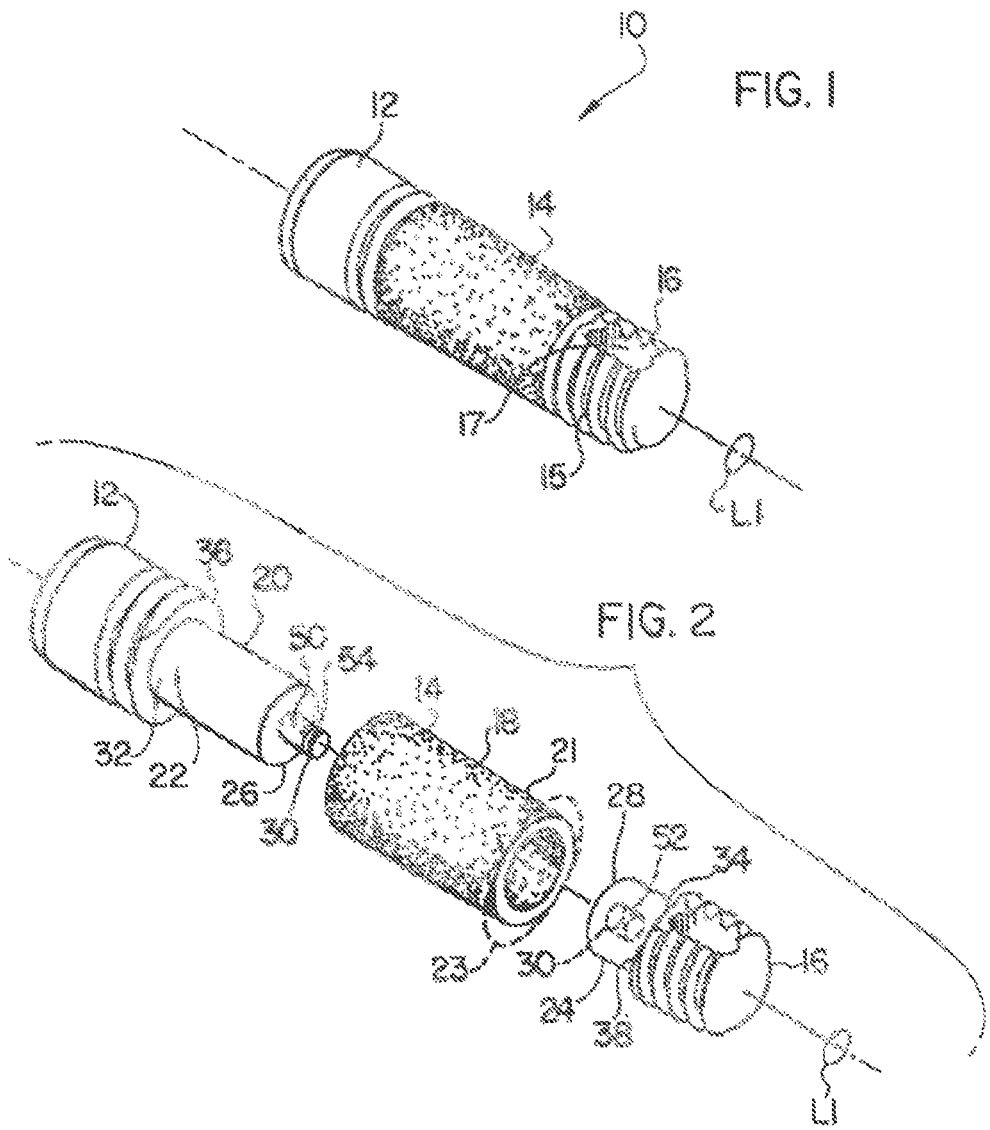

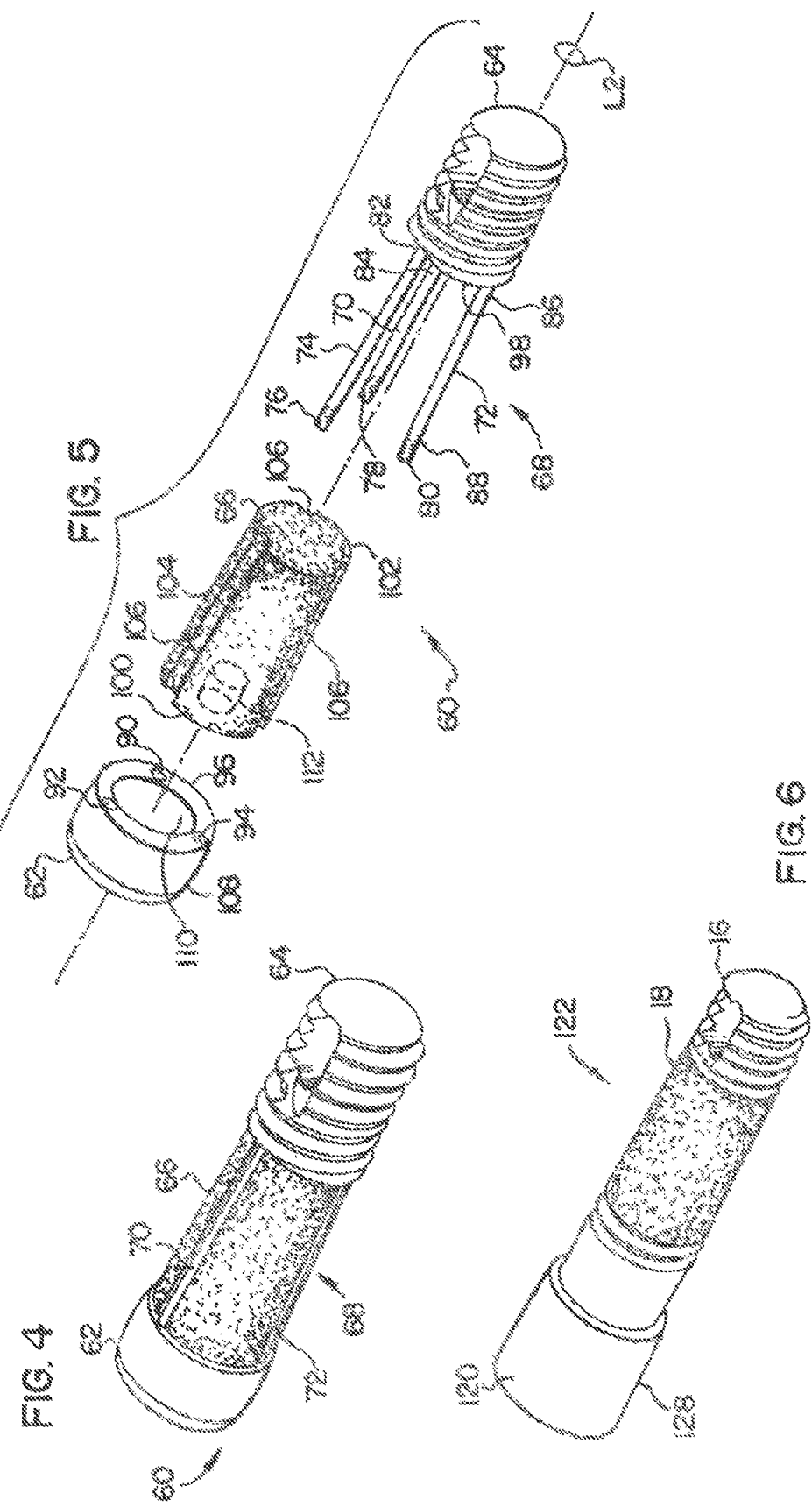

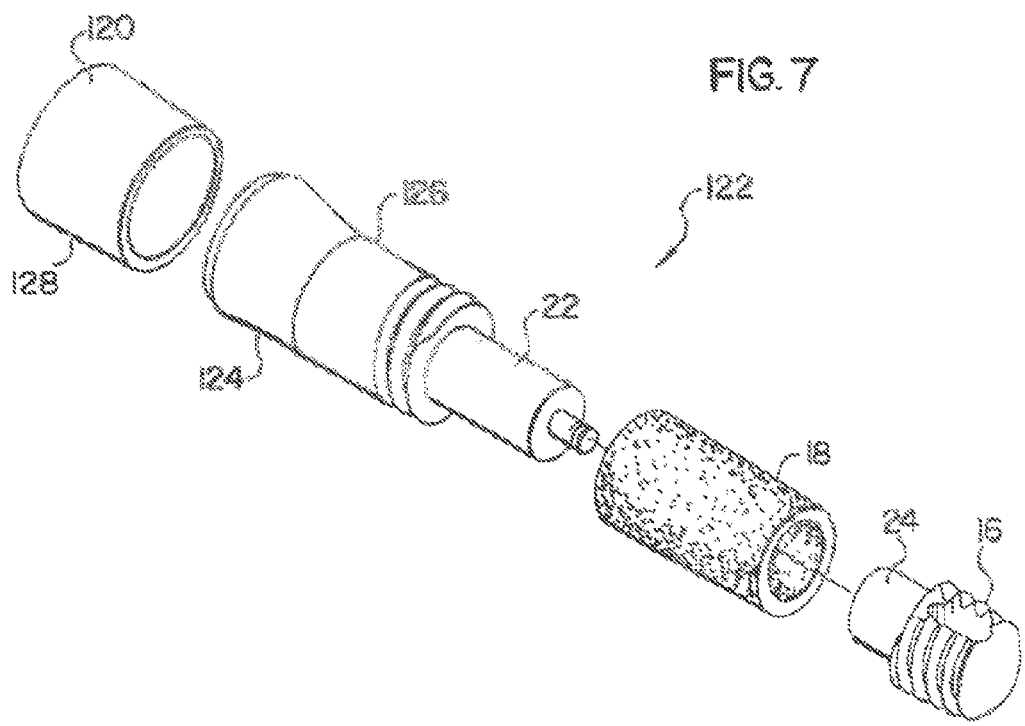

MODULAR IMPLANT WITH SECURED POROUS PORTION

CLAIM OF PRIORITY

This application is a continuation of U.S. patent application Ser. No. 12/167,088, filed on Jul. 2, 2008, the benefit of priority of which is claimed hereby, and is incorporated by reference herein in its entirety.

BACKGROUND OF THE INVENTION

1. Field of the Invention

The present invention relates to bone implants and, in particular, to a modular dental implant with structure for securing a porous portion to the implant.

2. Description of the Related Art

Dental implants are commonly used as anchoring members for dental restorations to provide prosthetic teeth at one or more edentulous sites in a patient's dentition at which the patient's original teeth have been lost or damaged. Known implant systems include a dental implant made from a suitable biocompatible material, such as titanium. The dental implant is threaded or press fit into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods.

Many current dental implant surgeries are performed in two stages. In the initial or first stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's bone grows around the implant to securely anchor the implant, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example. Alternative single stage implants may be used that extend through the transgingival layer so that the gingiva need not be reopened to access the implant.

One way to improve osseointegration onto the implant, and in turn long term stability of the implant, is to provide a porous material on the implant that the bone can grow into. Such a porous material may also increase short term stability for immediate loading because of its large friction coefficient with surrounding bone. Securing the porous material to the dental implant, however, may be difficult due to the small size and geometry of the device. In general, dental implants are 3 mm to 6 mm in diameter and 4 mm to 16 mm in length. If it is desired for the porous material to only cover a portion of the implant with the remainder being made up of, for example, reinforcing element, threads to compliment initial stability or interface geometry to secure a dental prosthesis, the porous section becomes too small to practically include threads or other securing geometry. Therefore, an implant is desired that includes a locking element to economically secure the porous material in place while allowing for other features such as threads, abutment interface geometry or reinforcing members.

BRIEF DESCRIPTION OF THE DRAWINGS

FIG. 1 is a perspective view of a dental implant with porous material in accordance with the present invention;

FIG. 2 is an exploded view of the dental implant of FIG. 1;

FIG. 3 is an enlarged fragmentary view of a porous tantalum portion for any of the embodiments herein and in accordance with the present invention;

FIG. 4 is a perspective view of a second embodiment of a dental implant in accordance with the present invention;

FIG. 5 is an exploded view of the dental implant of FIG. 4;

FIG. 6 is a perspective view of a third embodiment of a dental implant in accordance with the present invention;

FIG. 7 is an exploded view of the dental implant of FIG. 6; and

DETAILED DESCRIPTION

Figure 8:
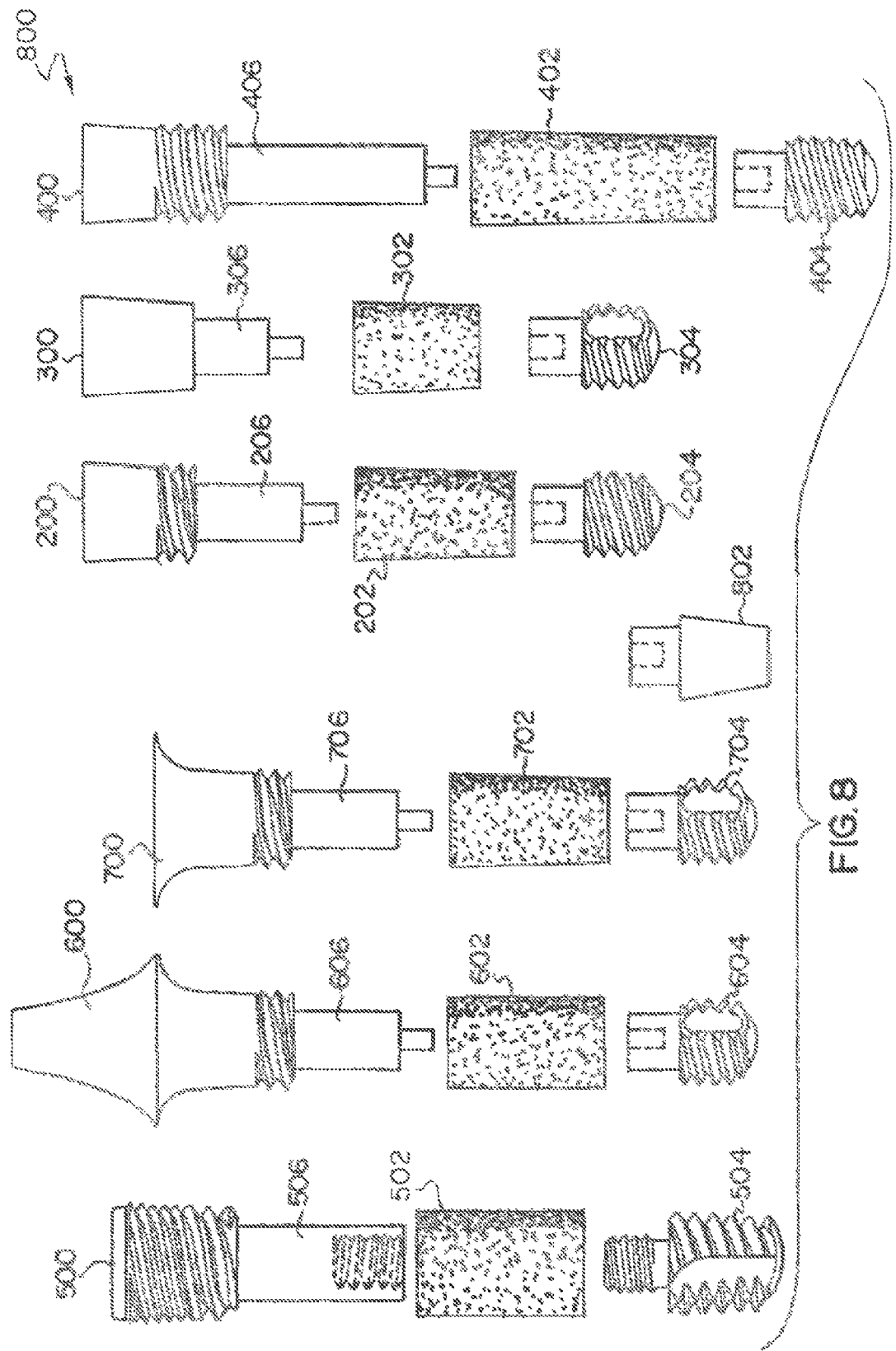
FIG. 8 is an exploded view of multiple alternative parts of a modular implant in accordance with the present invention.

Referring to FIG. 1, an implant 10 for placement in bone in one form, is a dental implant for insertion into a mandible or maxilla. The implant 10 comprises at least three pieces, but may include more pieces. The implant 10 is used to anchor a tooth abutment or other dental prosthesis and includes a coronal part or head 12, an intermediate part 14 for improving osseointegration onto the implant 10 as explained in greater detail below, and a separate stem, anchor, or apical part 16. The anchor 16 is configured to engage the head 12 so that at least the head 12 and the anchor 16 cooperatively secure the porous metal part 14 on the implant 10.

The head 12 and the anchor 16 may also comprise external threads 15 for engaging bone. Patients prefer to leave after initial surgery with some type of restoration, and healing of both soft and hard tissue may be improved if the implant is loaded after surgery. Post-surgical loading, even if less than a full load of occlusion however, is sufficient to displace the implant. Thus, self-tapping threads are used to achieve initial stability. Before osseointegration has time to take place, the thread resists tension, twisting or bending loads applied to the implant. Further, the anchor 16 may have an opening 17 for receiving bone chips while threading implant 10 into the bone. Alternatively, the implant may be without threads to be press fit into bone by a driver and as discussed further below.

In one form, implant 10 may have an outer diameter of approximately 3.0 mm to 6.0 mm and a length of approximately 8 mm to 16 mm. While the implant 10 may have a generally cylindrical outer surface, the implant 10 may also taper so that its diameter increases as it extends coronally to further increase friction with bone within a bore receiving the implant.

Referring to FIGS. 1-2, in the illustrated form, the porous part 14 includes a generally cylindrical sleeve portion 18 that receives and fits on a core 20 on the implant 10. The sleeve portion 18 has a thickness of about 0.020" to 0.050" and may taper to generally match the taper of the implant, if present. Alternatively, to increase the stability of the implant, the sleeve portion 18 may have an outer periphery or surface 23

(represented by dashed lines) that is non-cylindrical or non-circular (in transverse cross-section) rather than the circular outer surface 21 that is shown. In this case, the outer surface 23 of the sleeve portion 18 does not generally match the taper or outer periphery of the implant and does not match the shape of the bore it sits within. In this case, to further strengthen the fit between the implant and the bore in the jaw bone, the outer periphery 23 of the intermediate part 14 or sleeve portion 18 may be provided with a maximum width slightly greater than the diameter of the bore. So configured, as the implant device is inserted into the bore, the larger outer periphery roughened by the porous material will bite into the bone by grating, chipping and/or flaking bone pieces off of the sidewalls of the bore in which the implant device is being placed. When the implant is press-fit into the bore rather than threaded into the bore, this "rasping" action forms slight recesses or indents within the bore sidewall in which the implant device sits. This further restricts rotational or twisting motion of the implant device within the bore since the implant device does not have the clearance to rotate out of the indents and within the bore.

The rasping action also accelerates osseointegration onto the implant device and into the pores of the porous material due to the bone compaction into the pores. First, the grating of the bone structure causes the bone to bleed which stimulates bone growth by instigating production of beneficial cells such as osteoblasts and osteoclasts. Second, the bone pieces that fall into the pores on the porous material assist with bone remodeling. In the process of bone remodeling, osteoblast cells use the bone pieces as scaffolding and create new bone material around the bone pieces. Meanwhile osteoclast cells remove the bone pieces through resorption by breaking down bone and releasing minerals, such as calcium, from the bone pieces and back into the blood stream. The osteoblast cells will continue to replace the grated bone pieces from the pores and around the implant device with new and healthy bone within and surrounding the extraction site. Thus, with the porous material, the implant device has increased resistance to twisting or rotation, allows for immediate or very early loading, and increases long-term stability due to the improved osseointegration.

The transverse cross-section of the outer surface of the sleeve portion may have flat sides and may be polygonal, or may have curved sides such as with ovals, or may be any combination or variation thereof, whether or not a regular shape. The bore that receives such an implant may be cylindrical or any other desired predetermined shape. This applies to any of the intermediate portions described herein. The exemplary, and exaggerated, outer periphery 23 is shown to be oval.

When assembled, the core 20 extends axially from the head 12, the anchor 16, or both the head 12 and the anchor 16. Core 20 also may be integrally formed with, or otherwise permanently connected to, either the head 12 or anchor 16. Alternatively, core 20 may include both a coronal portion 22 which extends integrally from the head 12, and an apical portion 24 which extends integrally from the anchor 16. In this case, the coronal portion 22 and the apical portion 24 may have engaging distal ends 26 and 28 that form a locking mechanism 30 configured to secure the head 12 to the anchor 16. As another alternative, however, the core 20 may have one longitudinal end 32 integral with one of the head and anchors 12 and 16, and an opposite longitudinal end 34 forming locking mechanism 30 to engage with the other of the head 12 and anchor 16.

As yet another alternative, the core 20 is separate (or has a separate portion) from both the head 12 and the anchor 16. In this form, a locking mechanism 30 is formed at both opposite longitudinal ends 32 and 34 of the core (or at two other intermediate locations along the core).

To secure the sleeve portion 18 on the core 20, the head 12 and anchor 16 have a greater diameter than the core 20 such that the head 12 and the anchor 16 each have a retaining shoulder 36 and 38 that extends radially outward from the core 20 relative to a longitudinal axis L1 generally defined by the implant 10. The shoulders 36 and 38 face each other so that when sleeve portion 18 is assembled on the core 20, the sleeve portion 18 is retained between the shoulders 36 and 38.

In one form, the head 12, the anchor 16, and the core 20 (whether or not it is separate) are made of a suitable biocompatible material such as titanium, titanium alloy, stainless steel, zirconium, cobalt-chromium molybdenum alloy, polymers such as polyether ketone ketone (PEKK) for one example, ceramic, and/or composite material.

Referring to FIG. 3, the porous part 14 may include metal, and in one form, is a porous tantalum portion 40 which is a highly porous biomaterial useful as a bone substitute and/or cell and tissue receptive material. An example of such a material is produced using Trabecular Metal™ technology generally available from Zimmer, Inc. of Warsaw, Ind. Trabecular Metal™ is a trademark of Zimmer Technology, Inc. Such material may be formed from a reticulated vitreous carbon foam substrate which is infiltrated and coated with a biocompatible metal, such as tantalum, etc., by a chemical vapor deposition ("CVD") process in a manner disclosed in detail in U.S. Pat. No. 5,282,861, the disclosure of which is fully incorporated herein by reference. Other metals such as niobium, or alloys of tantalum and niobium with one another or with other metals may also be used.

As shown in FIG. 3, porous tantalum structure 40 includes a large plurality of ligaments 42 defining open spaces 44 therebetween, with each ligament 42 generally including a carbon core 46 covered by a thin film of metal 48 such as tantalum, for example. The open spaces 44 between ligaments 42 form a matrix of continuous channels having no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor implant 10 into the surrounding bone of a patient's jaw which increases stability. The rough exterior surface of such porous metal part has a relatively high friction coefficient with adjacent bone forming the bore that receives the implant to further increase initial stability as alluded to above. This structure can produce superior aesthetic results by restricting movement of the implant. These implants can be placed without supplementary surgical procedures, such as bone grafting, and can be placed in areas where traditional implants have been less successful, such as with reduced or decayed alveolar sections.

Porous tantalum structure 40 may be made in a variety of densities in order to selectively tailor the structure for particular applications. In particular, as discussed in the above-incorporated U.S. Pat. No. 5,282,861, the porous tantalum may be fabricated to virtually any desired porosity and pore size, whether uniform or varying, and can thus be matched with the surrounding natural bone in order to provide an improved matrix for bone in-growth and mineralization. This includes a gradation of pore size on a single implant such that pores are larger on an apical end to match cancellous bone, and smaller on a coronal end to match cortical bone, or even to receive soft tissue ingrowth. Also, the porous tantalum could be made denser with fewer pores in areas of high mechanical stress. Instead of smaller pores in the tantalum, this can also be accomplished by filling all, or some of the pores with a solid material which is described in further detail below.

To provide additional initial mechanical strength and stability to the porous structure, the porous structure may be infiltrated with a filler material such as a nonresorbable polymer or a resorbable polymer. Examples of non-resorbable polymers for infiltration of the porous structure may include a polyaryl ether ketone (PAEK) such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers may include polylactic co-glycolic acid (PLGA), polylactic acid (PLA), polyglycolic acid (PGA), polyhydroxybutyrate (PHB), and polyhydroxyvalerate (PHV), and copolymers thereof, polycaprolactone, polyanhydrides, and polyorthoesters. By providing additional initial mechanical strength and stability with a resorbable filler material, a titanium reinforcing implant core may not be required. The resorbable material would resorb as the bone grows in and replaces it, which maintains the strength and stability of the implant.

Referring again to FIGS. 1-2, the locking mechanism 30 may secure the head 12 and anchor 16 together by a threaded connection, press fit, or similar mechanisms. Thus, the locking mechanism 30 may include at least one axially extending post 50 on either the core portion 22 of the head 12 or core portion 24 of the anchor 16. An axially extending bore 52 (shown in dashed line) receives the post 50 on the other core portion 22 or 24. In the illustrated form, the post 50 may have threads 54 to match internal threads in bore 52. Otherwise, the post 50 may have a corresponding diameter to provide a tight friction fit to be press fit into bore 52. In one example, an anchor 504 has a threaded core portion 24 that fits into a bore on a core portion 22 extending from a head 500 (FIG. 8).

With this configuration, the head 12 and anchor 16 secure the sleeve portion 18 on the core 20 without other devices. It will be appreciated, however, that the sleeve portion 18 could additionally be dimensioned to have a friction fit on the core 20 to resist further axial and/or rotational movement of the sleeve portion 18 on the core 20. Other mechanisms, such as adhesive, welding, diffusion bonding, sintering, fasteners, and so forth may also be used to secure the sleeve portion 18 to the core 20.

It will also be understood that head 12 may have a male abutment connector on its coronal surface to connect to a separate abutment. Alternatively, the head 12 has a bore for receiving a portion of an abutment and/or an abutment anchor where such bore may also extend into the core 20.

Referring now to FIGS. 4-5, implant 60 has a similar basic structure to that of implant 10 including a head 62 and a anchor 64 that cooperatively secures a porous portion 66 to the implant 60. Like implant 10, implant 60 comprises at least three pieces, but may include more pieces. Porous portion 66 has the same or similar material as porous portion 14 on implant 10. A locking mechanism 68 secures the head 62 to the anchor 64. The locking mechanism 68 here, however, includes a plurality of locking members 70, 72 and 74 that extend axially from the head 62 and the anchor 64. Each locking member 70, 72 and 74 has an end portion 76, 78, 80, respectively, that engages the head 62, and respective end portions 82, 84, 86 that engage the anchor 64. In one form, the end portions 76, 78, 80 or end portions 82, 84, 86 are integrally formed with either the head 62 or anchor 64 while the opposite end portions are free ends that engage the head 62 or the anchor 64 by either a press fit or by a threaded connection with threads 88 (shown in dashed lines). In this case, the free end portions, whether configured for press-fit or threaded connections, are respectively received in bores 90, 92, and 94. It will be understood, however, that all of the end portions 76, 78, 80 and 82, 84, 86 may be free ends that fit into bores on both the head 62 and the anchor 64. If threaded connections are used, bores 90, 92, and 94 may be through bores so that the locking members 70, 72, and 74 may be independently rotated into place and anchored to stem 64 (or vice-versa).

In the illustrated form, the three locking members 70, 72, and 74 are uniformly, circumferentially spaced about central longitudinal axis L2, and the porous portion 66 is centrally located among the locking members 70, 72, and 74 so that the locking members restrict lateral movement of the porous portion 66 while interior faces 96 and 98 of the head and anchors 62 and 64, respectively, face or abut longitudinal ends 100 and 102 of the porous portion 66 to restrict axial movement of the porous portion 66.

To further restrict rotational and lateral movement of the porous portion 66, the porous portion 66 may have an outer surface 104 defining at least one longitudinally extending groove 106 for receiving the locking members 70, 72 and 74. In the illustration, the outer surface 104 defines a groove 106 for each locking member 70, 72 and 74.

The porous portion 66 separates the head 62 from the anchor 64 except for the locking members 70, 72 and 74. The porous portion 66 may be a bulk piece that is substantially porous. When implant 60 has a taper, the exterior surface 104 and/or the locking members 70, 72, and 74 may be inclined to match the slope of the taper. For this purpose, the locking members 70, 72, and 74 may also extend radially outwardly as the locking members 70, 72 and 74 extend coronally. It will be understood that instead, the locking members 70, 72 and 74 may remain parallel to axis L2 while the outer surface 104 tapers, or vice versa.

It will be appreciated that the locking mechanism 68 may have as few as one off-center locking member or more than three locking members whether or not uniformly spaced from and/or about longitudinal axis L2.

It will also be understood that while the locking mechanism 68 may secure the porous portion 66 to the implant 60 alone, adhesive, welding, diffusion bonding, sintering, fasteners and the like between the porous portion 66 and the locking members 70, 72 and 74, head 62 and/or anchor 64 may also be used.

The head 62 of implant 60 may include a collar 108. The collar 108 forms face 96 as an apically facing annular side. An interior surface 110 formed by a collar 108 extends coronally from the face 96 and is configured for receiving an abutment connector. Porous portion 66 may have a corresponding bore 112 (shown in dashed line) that aligns with interior surface 110 to receive a portion of a separate abutment and/or an abutment connector. The bore 112 may or may not be threaded. Alternatively, the head 12 includes male structure to mount a separate abutment.

Implant 60 may be an externally threaded implant rather than a press fit implant. In this case, anchor 64 may have similar structure as that of anchor 16 on the implant 10 relating to threading and self-tapping. While the collar 108 is shown without external threads, it will be understood that such threads could be provided.

It will be understood that porous portions 14 and 66 could be formed with external threads that are continuous with threads of the head and/or anchors. With implant 60, the locking members 70, 72 and 74 may or may not have shapes to match the threads.

It will also be appreciated that for any of the configurations herein, the intermediate sleeve or bulk material may be made of, or include, materials that promote bone growth or increase the strength of the implant other than porous tantalum. Such materials include organic bone graft (e.g., autograft, allograft, xenograft), resorbable polymer (e.g., polylactic co-glycolic acid (PLGA), polylactic acid (PLA), polyglycolic acid (PGA), polyhydroxybutyrate (PHB), and polyhydroxyvalerate (PHV)), non-resorbable polymer, synthetic bone material such as hydroxyapatite (HA), or collagen.

Referring to FIGS. 6 and 7, a collar 120 may optionally be used on an implant 122. While implant 122 may be similar to implant 10 of FIG. 1 or implant 60 of FIG. 4, implant 122 is shown here to be a single-stage surgery implant with an integral transgingival region 124. Otherwise, similar features are numbered the same as with the other implants. Collar 120 may be mounted on a head 126 by press fit, threading, adhesive, welding, connectors and so forth. The collar 120 may be a separate component from the head 126 or the collar 120 may be a surface treatment. The collar 120 may also be built-in to the head 126, i.e. the entire head 126 would be made up of the same material as the collar 120. The collar 120 has an exterior surface 128 configured to promote soft tissue attachment and may be made of high density polyethylene (HDPE), polyester, zirconium, ceramic or other similar surface treatments.

Referring to FIG. 8, in another aspect of the implants described herein, an extremely versatile, modular implant provides many different alternative parts so that a patient can receive an implant with a particular configuration that best matches the needs for his or her particular dental implant site. For this purpose, at least one of the head, the intermediate part, and the anchor of the implant is provided in a plurality of forms, and each form is configured to be assembled on at least one form of the other two of the head, intermediate part, and anchor. Thus, all three parts—the head, the intermediate part, and the anchor—can be independently selected among a plurality of different forms available for each part. Such parts may need to be ordered from a lab or manufacturing plant, or alternative forms may be provided to the practitioner in a kit, such as the example kit 800 illustrated in FIG. 8, that includes a set of alternative implant parts for each main part of the implant: the head, the intermediate part, and the anchor. In the example kit, a number of the head forms will fit on a number of different intermediate parts and a number of different anchors. Here, kit 800 includes heads 200, 300, 400, 500, 600, and 700; intermediate parts 202, 302, 402, 502, 602, and 702; and anchors 204, 304, 404, 504, 604, and 704 described in further detail below.

The plurality of forms represent differences for the parts that fall into three general categories: (1) shape and size, (2) material forming the part, and (3) exterior surface. Regarding size for all three main parts, the implants generally define a coronal-apical direction, and the plurality of forms provide forms of different sizes comprising at least one of various (1) coronal-apical lengths, (2) widths extending transverse to the coronal-apical direction, and (3) a combination of (1) and (2). For example, head 400 is longer than heads 200 and 300. intermediate part 302, and in turn core 306 extending from head 300, is shorter than intermediate parts 202 and 402. Intermediate parts 502 and 602 are wider than intermediate part 402, and so forth. It will be understood that while a main head body 208 and 308 has the same length, such as with heads 200 and 300 respectively, the lengths of the cores 206, 306, 406, 606, and/or 706 can have different lengths that correspond to the lengths of the intermediate parts 202, 302, 402, 502, 602, and 702 respectively that the cores will hold.

As to shape, for the heads, this may refer to the different platforms provided such as (1) a bone-level head (for a two-stage implant) 200, 300, 400, or 500 with a coronal end configured to be disposed at a crest of a mandible or maxilla; (2) a transgingival head (for a single-stage implant) 700 with a coronal section configured to extend through the gingiva; and (3) a one-piece implant head 600 that has an integral abutment. For the anchor, and the head, this may refer to whether or not the part is threaded, as with the anchors 204 and 304, for example, or has no threads for being press-fit as with the anchor 802. The anchor may or may not have a self-tapping cutting edge and hole or vent for receiving bone chips.

For two-stage and single-stage implant heads, the heads may also provide different abutment connections associated with them (e.g., internal hex, external hex, spline, angled connection, etc.).

For the intermediate part, alternative cross-sectional shapes with outer peripheries may be non-circular to increase friction as described above. The alternative forms provided may include circular shapes, non-circular curved shapes such as ovals, ellipses, and so forth, polygonal shapes such as hexagons whether regularly shaped or not, and any combination of both curves and flat sides. Alternative intermediate part forms may provide at least two different longitudinal taper angles such as that seen by a comparison of the intermediate parts 202 and 702, or at least one no-taper option may be provided as with the intermediate parts 502 and 602.

For the second category of differing materials, the intermediate part may be provided in forms that have at least two different materials. This may include (a) a porous material, (b) a porous metal, (c) a porous metal including tantalum, (d) a ceramic, (e) a metal, (f) a polymer, (g) a resorbable material, (h) a non-resorbable material, (i) organic bone graft, (j) synthetic bone material, and (k) collagen. The heads may be made of two different materials and may include (a) titanium, (b) zirconia, (c) an esthetic material and/or a (d) composite material.

For the third category, the head may have a surface coating, surface roughening by using microthreads or surface blasting, a polished collar, and/or a biological coating as mentioned above. As also mentioned above, the porous material of the intermediate part provides for the ingrowth of bone or soft tissue, and may have varying pore size or filler placement.

Figure 9:
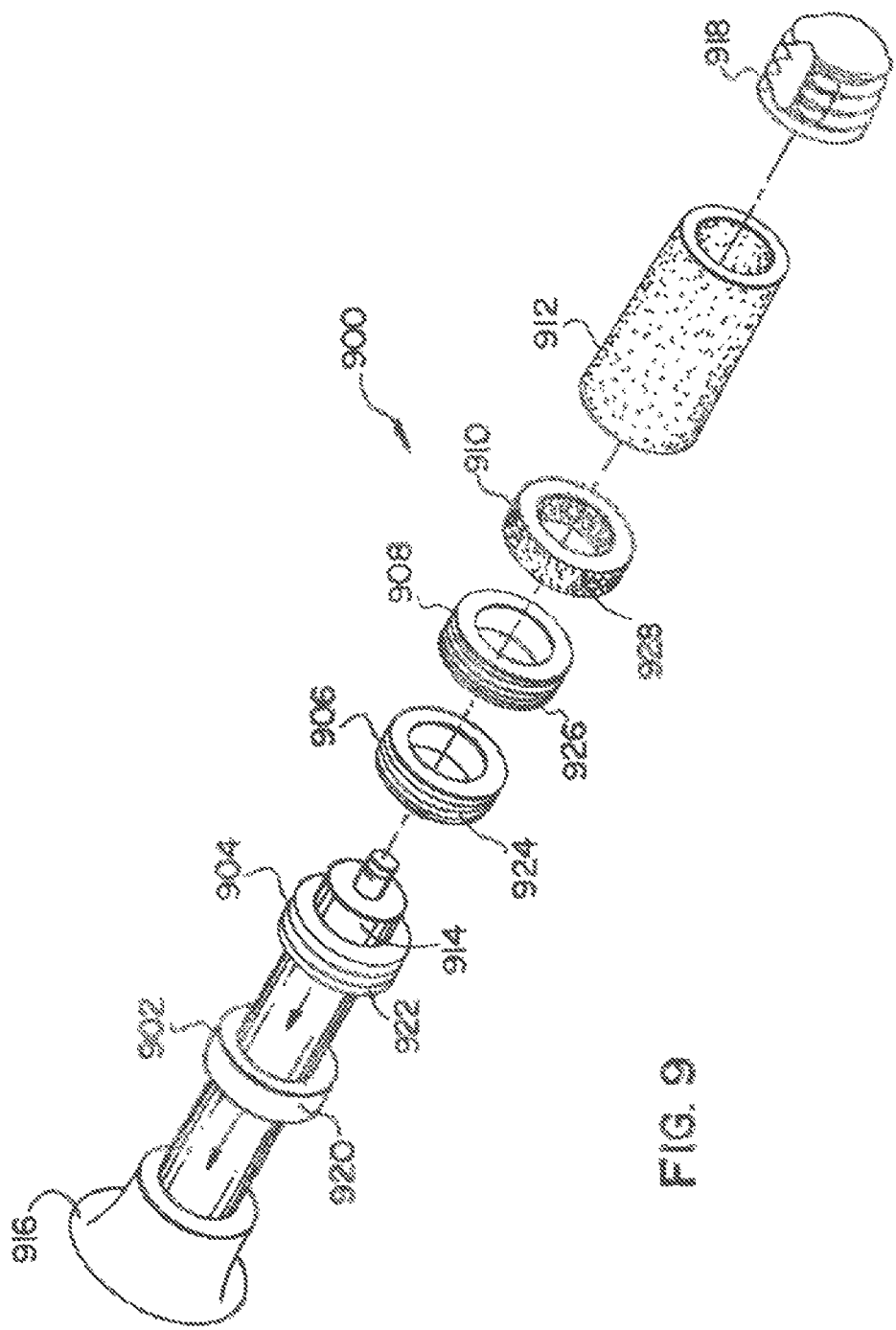
FIG. 9 is an exploded, perspective view of another modular implant with stacked portions.

Referring to FIG. 9, in an expansion of this third category, the implants may include a plurality of separate stacking pieces where each stacking piece has a specific type of exterior surface. Since soft and hard tissues respond differently to implants than to natural teeth, the objective of such a zoned implant is to stimulate varied tissue responses similar to that of tissues adjacent to natural teeth. The different stacking pieces can create multiple zones to address the various multiple layers of tissue (e.g., crestal or cortical bone, cancellous bone, prevention of soft tissue downgrowth, soft tissue attachment, prevention of epithelial downgrowth, and bacterial removal). Thus, each of the stacking pieces may be made of a different exterior material or have a different surface coating or texture to address the different layers of opposing tissue.

In one example, the stacking pieces are selectively mountable in a variety of sequences for best matching the anatomy of the dental site, each stacking piece providing a different exterior surface than at least one exterior surface on other stacking pieces on the same implant. Specifically, for example implant 900, stacking pieces 902, 904, 906, 908, and 910, as well as a porous intermediate part 912 are mounted on a core 914 of a head 916. The head 916 connects to an anchor 918 at the core 914 to secure the stacking pieces 902, 904, 906, 908, and 910 and the intermediate part 912 on the implant 900. The stacking pieces 902, 904, 906, 908, and 910 may be ring shaped but other shapes are possible such as penannular, or other nonannular shapes that have tab and groove connections with the core 914, for example. As described herein, the stacking pieces may be considered to be a portion of the head, a portion of the intermediate part, a portion of both, or considered as separate from both. While the illustrated stacking pieces 902, 904, 906, 908, and 910 are placed between the intermediate part 912 and the head 916, the stacking pieces 902, 904, 906, 908, and 910 may also be placed below the intermediate part 912.

In the illustrated form, implant 900 is a single stage implant such that head 912 flares outward as it extends coronally and transgingivally to generally match the flare of a natural tooth. In the transgingival section of the head 912, the stacking pieces 902, 904, 906, 908, and 910 may have increasing larger diameters, if desired, to correspond to the dimensions of the outward flare.

To provide a surface configured to be easily cleaned of bacteria and placed supragingivally on the coronal end of the implant 900, the exterior surfaces 920 of the available stacking pieces 902, for example, may provide a smooth, machined metal surface such as Titanium. Such stacking pieces may also incorporate transition metal ions such as Ag, Cu, Zn, bactericidal polymers, antibiotic coatings, and/or nanoscale surface roughness that prevents colonization of bacteria on the exterior surface. Such anti-bacterial treatments may also be placed more apically on the implant as desired. Such stacking pieces may also be made of ceramic or polymers instead of, or in addition to, metals.

Stacking pieces 904 directed to promotion of an epithelial barrier may have alternate exterior surfaces 922 that include micron scale surface texturing such as contoured grooves, dot matrix, and/or discontinuous horizontal lines that allow fiber alignment and attachment onto the geometry to create a seal. For instance, microgrooves approximately 20 μm deep and approximately 20-40 μm wide have been shown to block epithelial down growth via connective tissue cells that orient so as to insert into the implant surface. Contact guidance is made by cells bridging over the grooves rather than the cells aligning within the grooves as with larger size grooves. The stacking may also or alternatively have coatings such as collagen to activate type 1 contact inhibition, and/or patterned surface properties that selectively alter the surface wettability to orient the epithelial cell attachment, via haptotaxis, to prevent epithelial down growth.

Stacking pieces 906 directed to the promotion of soft tissue formation may have alternate exterior surfaces 924 with nanotextures or microtextures that also allow for fiber insertion into microscale geometry as mentioned above for the epithelial barrier or have larger grooves to align the cells of the soft tissue. The stacking pieces may also have surface coatings such as collagen, growth factors, or peptides. The stacking pieces could also have the porous material, including tantalum in one example as mentioned herein with pores sized to promote soft tissue ingrowth.

Stacking pieces 908 directed to the promotion of a soft tissue barrier to limit soft tissue migration into the gap between the alveolar and the implant may have alternate exterior surfaces 926 with collagen coating to activate type 1 contact inhibition, a collagen membrane (durable or degradable), increased calcium concentration, and/or a demineralised bone matrix. The stacking pieces may also have texturing or micropatterning that gingival tissue cannot cross such as circumferential grooves, discontinuous horizontal lines, or other alternate shapes. The exterior surfaces of the stacking pieces may also have patterned surface properties such as selectively altered surface wettability to orient the gingival cell attachment, via haptotaxis, to prevent gingival down growth.

Stacking pieces 910 directed to the promotion of cortical bone growth may have alternate exterior surfaces 928 made of the porous materials or porous tantalum mentioned herein to mimic the bone structure and allow ingrowth. Such materials or other materials that create pores or surfaces for ingrowth should have a modulus similar to the adjacent cortical bone to limit stress shielding. Surface treatments used to increase the rate of cortical osseointegration onto the exterior surfaces include nanotexturing, microtexturing, and/or surface coatings of magnesium, calcium, phosphate, and bioactive coatings with growth factors and/or peptides.

Stacking pieces or intermediate part 912 directed to the promotion of cancellous bone growth may be made of a porous material such as the porous metal or porous tantalum described above. A number of stacking pieces may be provided with different pore sizes to generally correspond to standard, microscopic alveolar structure.

While in the illustrated structure, one stacking piece for each category (anti-bacterial, epithelial barrier, soft tissue growth, soft tissue barrier, cortical bone ingrowth) would be selected while a bulk intermediate part would be selected for cancellous bone ingrowth, it will be understood that many different combinations can be selected depending on the needs of the patient's dental site.

In one form the stacking pieces for a particular implant will all have the same thicknesses (in the coronal-apical direction). In another form, the stacking pieces will have a thickness that best matches a standard or typical thickness of the anatomy it is to be placed against. Alternatively, different thicknesses may be provided for each category of exterior surface or anatomy the stacking piece is to be placed against so that the doctor can choose the closest match. Alternatively, the stacking pieces may be ordered on a custom or patient specific basis such that the thicknesses of the stacking pieces are set to match a particular patient's anatomy as explained in greater detail below.

It will also be appreciated that a stacking piece may have two or more different exterior surfaces either axially (in the coronal-apical direction) or circumferentially spaced, or two or more stacking pieces with the same exterior surface may be placed on the same implant to increase the height for that type of selected exterior surface. Stacking pieces with similar exterior surfaces may be placed on both the apical and coronal sides of a stacking piece with a different exterior surface to create a barrier at a certain location along the implant.

Any of the parts mentioned above (the head, the intermediate part, the anchor, and/or the stacking pieces) with any of the characteristics mentioned above can be stock components that are pre-assembled in-house. Alternatively, the stock components can also be shipped separately to the doctor for him or her to assemble chair-side during surgery, allowing the clinician to choose the most appropriate parts when the dental site is accessible. One or more stock parts may be provided in a kit or may be ordered individually.

Optionally, in addition to, or instead of, stock implant parts, the implant parts can be customized to correspond to the exact dimensions of a patient. For instance, a custom head may have a platform, dimensions, materials, and/or exterior surfaces that are configured to match the exact dimensions of a patient's anatomy. Such a patient-specific custom-ordered head can be mounted on a number of different modular intermediate parts and anchors because the head has the same general interface for assembly with the intermediate part and anchor, as explained above.

To accomplish this customization, imaging technologies that allow CAT scan, radiographic, or visible light scan of the jaw and dentition have been combined with computer aided design ("CAD"), computer aided manufacturing ("CAM"), and rapid prototyping technologies to make Patient-Specific dental products. These technologies can be used to shape and size the implant parts as described herein to better correspond to patient specific anatomy and that will integrate better into the human body.

The patient-specific customization also applies to the anchor and/or the intermediate part. The anchor and intermediate part may be provided with particular dimensions or shapes to correspond to the dimensions of a bore at a patient's implant site. The anchor and any apical threads may be designed on a case-by-case basis also. For example, a clinician may want a modular implant with no apical threads. Further, the clinician may want the implant (the head, intermediate part, and anchor) to be made entirely of porous material or another material. Exterior surfaces on the intermediate part and anchor may also be customized as mentioned above.

With the structures described above, and whether or not stock parts or customized parts are used, the doctor is able to select a desired form for at least one of the head, the intermediate part, and the anchor for the modular implant, and make the selection specifically for a particular examined patient site to receive the modular implant. In one case, the form of each of the head, intermediate part, and the anchor are selected specifically for the particular examined patient site, and yet in another case, stacking pieces are also used on the implant and selected with the particular patient site in mind.

As another option, at least one of the head, the intermediate part, and the anchor is customized for a particular patient to receive the modular implant. In some of these cases, at least one of the parts may be a non-customized stock part.

If the clinician decides to assemble and place the implant chair-side, another feature of the modularity is to be able to place the anchor with or without the intermediate part first, place a healing screw, and cover it over for healing while a patient-specific implant head is being manufactured. When the patient-specific implant head is completed, the clinician can then revisit the surgical site, remove the healing screw, and attach the customized patient-specific implant head. In this situation, the implant is assembled in-vivo and is designed and customized specifically for a particular patient's bone and soft tissue anatomy.

Also, a modular implant can have the advantage of easier replacement or revision in certain cases if the implant fractures or otherwise fails. In this situation, instead of having to remove and replace the entire implant, the clinician may only need to remove and replace the head, where most fractures or failures would generally occur. In this way, the anchor and the intermediate part remains completely osseointegrated and stable during and after replacement of the head while the tissue heals.

While the illustrated forms are shown to be dental implants, it will be understood that such structures, with modular implants with interchangeable parts as described above and where an intermediate part is secured to the implant by a head and an anchor, may be applied to implants used on other areas of a human or animal body.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A modular implant system, comprising:
   a plurality of heads having a plurality of different head forms each head form configured for supporting a dental prosthesis and at least one of the different head forms having an apical end with an exterior threaded portion configured for engaging bone;
   a plurality of porous intermediate sleeves having a plurality of different intermediate sleeve forms configured for engaging bone, wherein at least one of the plurality of intermediate sleeve forms is configured to be assembled on at least one of the plurality of different head forms; and
   a plurality of initially separate anchors having a plurality of different anchor forms, wherein at least one of the plurality of anchor forms is configured to engage at least one of the plurality of head forms of the head so that at least one of the plurality of head forms and at least one of the plurality of anchor forms can cooperatively secure at least one of the plurality of intermediate sleeve forms of the intermediate sleeve to form a modular implant.

2. The modular implant system of claim 1, wherein the plurality of heads include at least one externally threaded head and at least one press-fit head.

3. The modular implant system of claim 1, wherein each of the plurality of intermediate sleeve forms is at least partially formed from one or more of:
   a porous metal,
   a porous metal including tantalum,
   a ceramic,
   a metal,
   a polymer,
   a resorbable material,
   a non-resorbable material,
   an organic bone graft,
   a synthetic bone material, and
   a collagen.

4. The modular implant system of claim 1, wherein each of the plurality of head forms is at least partially formed from one or more of:
   titanium,
   zirconia,
   an esthetic material,
   a composite material,
   a surface coating,
   microthreads,
   a polished collar, and
   a biological coating.

5. The modular implant system of claim 1, wherein the plurality of intermediate sleeve forms each have an intermediate cross-sectional shape with an outer periphery forming at least one of:
   (1) a non-circular curved shape,
   (2) a polygonal shape,
   (3) both (1) and (2), and
   (4) an irregular shape having at least one flat side and at least one curved side.

6. The modular implant system of claim 1, wherein the plurality of at least one of the head, the intermediate sleeve, and the anchor is configured to provide an exterior surface configuration for the implant including:

a surface configured to be easily cleaned of bacteria,
a surface that promotes formation of an epithelial barrier,
a surface that promotes soft tissue formation,
a surface that promotes a soft tissue barrier,
a surface that promotes cortical bone growth, and
a surface that promotes cancellous bone growth.

7. The modular implant system of claim 1, wherein each of the plurality of intermediate sleeve forms defines a longitudinal taper angle, including a taper angle of zero degrees.

8. The modular implant system of claim 1, further comprising:
a plurality of cores, each of the cores configured to extend axially from at least one of the pluralities of heads and anchors; and
a locking mechanism being formed on each core of the plurality of cores, the locking mechanism configured to secure the head to the anchor,
wherein a length of each core corresponds to a length of a corresponding intermediate sleeve.

9. The modular implant system of claim 8, wherein the locking mechanism includes a post formed on an apical portion of each of the plurality of cores, the post configured to be received by a coronally accessible bore in the anchor.

10. The modular implant system of claim 9, wherein the post and anchor include corresponding threads.

11. The modular implant system of claim 8, wherein the locking mechanism includes an apically accessible bore configured to receive an anchor post formed on the anchor.

12. The modular implant system of claim 1, wherein at least one of the intermediate sleeve forms, the head forms, and the anchor forms is configured to be selected for a specific examined patient site to receive the modular implant.

13. The modular implant system of claim 1, wherein one of the plurality of heads is assembled to one of the plurality of intermediate sleeves and one of the plurality of anchors after the intermediate sleeve and the anchor are implanted.

14. The modular implant system of claim 1, wherein each of the plurality of anchors includes an opening configured to receive at least one of a bone chip and tissue when the modular implant is inserted in a patient site.

15. The modular implant system of claim 1, wherein the plurality of head forms include:
a bone-level head with a coronal end configured to be disposed at a crest of a mandible or a maxilla;
a transgingival head with a coronal section configured to extend through gingiva; and
a one-piece implant head comprising a portion configured for engaging the intermediate sleeve and having an integral abutment formed thereon.

16. The modular implant system of claim 1, wherein the at least one of the plurality of head forms, the at least one of the plurality of intermediate sleeve forms, and the at least one of the plurality of anchor forms, when assembled, are configured to define a specified coronal-apical length of the modular implant.

17. The modular implant system of claim 1, wherein the plurality of head and anchor forms each include a different material.

* * * * *